US008501232B2

(12) United States Patent
Talton et al.

(10) Patent No.: US 8,501,232 B2
(45) Date of Patent: Aug. 6, 2013

(54) PROCESS OF FORMING AND MODIFYING PARTICLES AND COMPOSITIONS PRODUCED THEREBY

(75) Inventors: James D. Talton, Gainesville, FL (US); Christopher McConville, Sugarland, TX (US)

(73) Assignee: Nanotherapeutics, Inc., Alachua, FL (US)

( * ) Notice: Subject to any disclaimer, the term of this patent is extended or adjusted under 35 U.S.C. 154(b) by 1505 days.

(21) Appl. No.: 10/512,345

(22) PCT Filed: Apr. 23, 2003

(86) PCT No.: PCT/US03/11488
§ 371 (c)(1),
(2), (4) Date: Apr. 19, 2005

(87) PCT Pub. No.: WO03/090717
PCT Pub. Date: Nov. 6, 2003

(65) Prior Publication Data
US 2005/0175707 A1  Aug. 11, 2005

Related U.S. Application Data

(60) Provisional application No. 60/374,844, filed on Apr. 23, 2002.

(51) Int. Cl.
*A61K 9/14* (2006.01)
(52) U.S. Cl.
USPC .............................................. 424/489; 264/5
(58) Field of Classification Search
None
See application file for complete search history.

(56) References Cited

U.S. PATENT DOCUMENTS

| | | | |
|---|---|---|---|
| 3,608,715 A * | 9/1971 | Snyder et al. | 209/590 |
| 4,127,624 A | 11/1978 | Keller et al. | |
| 4,349,542 A * | 9/1982 | Staniforth | 424/679 |
| RE31,609 E | 6/1984 | Sears | |
| 4,525,339 A | 6/1985 | Behl et al. | |
| 4,722,941 A | 2/1988 | Eckert et al. | |
| 4,844,888 A | 7/1989 | Zawadzki | |
| 4,957,656 A | 9/1990 | Cerny et al. | |
| 5,145,684 A | 9/1992 | Liversidge et al. | |
| 5,190,748 A | 3/1993 | Bachynsky et al. | |
| 5,318,781 A | 6/1994 | Shah et al. | |
| 5,560,933 A | 10/1996 | Soon-Shiong et al. | |
| 5,801,106 A | 9/1998 | Jameson | |
| 5,916,596 A * | 6/1999 | Desai et al. | 424/489 |
| 5,958,452 A | 9/1999 | Oshlack et al. | |
| 5,981,719 A | 11/1999 | Woiszwillo et al. | |
| 5,997,812 A * | 12/1999 | Burnham et al. | 422/24 |
| 5,997,848 A | 12/1999 | Patton et al. | |
| 6,063,138 A | 5/2000 | Hanna et al. | |
| 6,190,699 B1 | 2/2001 | Luzzi et al. | |
| 6,197,346 B1 | 3/2001 | Mathiowitz et al. | |
| 6,217,908 B1 | 4/2001 | Mathiowitz et al. | |
| 6,235,313 B1 | 5/2001 | Mathiowitz et al. | |
| 6,248,360 B1 | 6/2001 | Choi et al. | |
| 6,258,341 B1 | 7/2001 | Foster et al. | |
| 6,261,599 B1 | 7/2001 | Oshlack et al. | |
| 6,303,149 B1 * | 10/2001 | Magdassi et al. | 424/489 |
| 6,309,671 B1 | 10/2001 | Foster et al. | |
| 6,368,586 B1 | 4/2002 | Jacob et al. | |
| 6,406,745 B1 | 6/2002 | Talton | |
| 6,428,814 B1 | 8/2002 | Bosch et al. | |
| 6,743,442 B2 | 6/2004 | Oshlack et al. | |
| 7,316,821 B2 | 1/2008 | Oshlack et al. | |
| 7,384,653 B2 | 6/2008 | Wright, IV et al. | |

OTHER PUBLICATIONS

Stemmer et al., "Organic Matter and Enzyme Activity in Particle-Size Fractions of Soils Obtained After Low-Energy Sonication", 1998, Soil Biol. Biochem., vol. 30, No. 1, pp. 9-17.*
Russell et al., "Sonic Energy in Processing: Use of a Large-Scale, Low-Frequency Sonic Reactor", 1999, Advances in Sonochemistry, vol. 5, pp. 279-302.*
Co-pending U.S. Appl. No. 12/202,881 entitled Compositions and Methods for Delivery of Poorly Soluble Drugs, filed Sep. 2, 2008.
DeJaeghere et al., *AAPS Pharmsci*, 3(1):1-8, Article 8 (2001).
De Jaeghere et al., *J. Controlled Release*, 68:291-298 (2000).
Adler et al., Stability and surface activity of lactate dehydrogenase in spray-dried trehalose, *J. Pharm. Sci.* 88:199-208 (1999).
Bartus et al., Sustained delivery of proteins for novel therapeutic agents, *Science* 281:1161-1162 (1998).
Cleland et al., Stable formulations of recombinant human growth hormone and interferon-gamma for microencapsulation in biodegradable microspheres, *Pharm. Res.* 13:1464-1475 (1996).

(Continued)

*Primary Examiner* — Robert A Wax
*Assistant Examiner* — Randeep Singh
(74) *Attorney, Agent, or Firm* — Finnegan, Henderson, Farabow, Garrett & Dunner, LLP (57) ABSTRACT

The present invention relates to processes for forming particles including drugs in a solution, changing the bulk or surface properties of a drug particle, and/or microencapsulating drug particles, and compositions produced thereby. In some embodiments, the process described utilizes mechanical agitation, more specifically low-frequency sonication, under controlled conditions, which provides mild shear forces during forming and/or precipitation to control the particle growth and mixing properties. Particle size can range from less than about 200 nanometers to greater than about one millimeter, depending on the processing conditions and application. This process, and the compositions produced, provide significant advantages in the manufacture of pharmaceutical particulate formulations, as well as biomedical, diagnostic, and chromatography particulate compositions, where sensitive macromolecules, such as proteins or DNA, are involved that would be degraded using more rigorous processing conditions or temperatures.

20 Claims, 5 Drawing Sheets

OTHER PUBLICATIONS

Cleland et al., The stability of recombinant human growth hormone in poly(lactic-co-glycolic acid) (PLGA) microspheres, *Pharm. Res.* 14:420-425 (1997).

Elsner at al., Ultrasonic degradation of DNA, *DNA*, 8:697-701, 1989.

Na et al., Physical stability of ethyl diatrizoate nanocrystalline suspension in steam sterilization, *Pharm. Res.* 16:569-574 (1999).

Niemi et al., The influence of ageing on the release of hydrocortisone from o/w creams, *Acta. Pharm. Nord.* 2:21-30 (1990).

Palakodaty et al., Phase behavioral effects on particle formation processes using supercritical fluids, *Pharm. Res.* 16:976-985 (1999).

Stahl et al., The effect of process variables on the degradation and physical properties of spray dried insulin intended for inhalation, *Int. J. Pharm.* 233:227-237 (2002).

Suslick et al., On the origin of sonoluminescence and sonochemistry, *Ultrasonics* 28:280-290 (1990).

Suzuki et al., A nifedipine coground mixture with sodium deoxycholate. II. Dissolution characteristics and stability, *Drug Dev. Ind. Pharm.* 27:951-958 (2001).

Williams et al., Moisture uptake and its influence on pressurized metered-dose inhalers, *Pharm. Dev. Technol.* 5:153-162 (2000).

International Search Report for PCT/US03/11488 (corresponding to U.S. Appl. No. 10/512,345) dated Aug. 19, 2003.

\* cited by examiner

PROCESS OF FORMING AND MODIFYING PARTICLES AND COMPOSITIONS PRODUCED THEREBY

RELATED APPLICATIONS

The present application claims priority under 35 U.S.C. §119 to U.S. Provisional Patent Application No. 60/374,844, filed Apr. 23, 2002. The entire contents of the aforementioned application is specifically incorporated herein by reference in its entirety.

GOVERNMENT INTERESTS

The United States government has certain rights to this invention by virtue of NASA contract No. NAS9-00121 and NIH grant No. 1R41DA14459-01.

II. BACKGROUND OF THE INVENTION

1. Field of the Invention

The present invention relates to processes for forming particles including drugs in a solution, changing the bulk or surface properties of a drug particle, and/or microencapsulating drug particles, and compositions produced thereby. In some embodiments, the process described utilizes mechanical agitation, more specifically low-frequency sonication, under controlled conditions, which provides mild shear forces during forming and/or precipitation to control the particle growth and mixing properties. Particle size can range from <200 nanometers to greater than one millimeter, depending on the processing conditions and application. The process described can be used to form a drug particle suspension, dry a wet powder slurry or suspension, as well as to improve the surface properties of the particle through conditioning the structure of the particle or particle surface and/or annealing the particle or particle surface. Annealing or conditioning drug particles may be used to force an amorphous to crystalline transition, creating a more stable powder, or smooth a particle surface. In addition, the process can be used to microencapsulate particles by suspending the microparticles in a non-solvent including a coating material (such as a biodegradable polymer) under controlled process conditions. The powder compositions produced thereby possess improved properties including, but not limited to, improved flow and dispersibility, controlled bioadhesion, stability, resistance to moisture, dissolution/release profiles, and/or bioavailabilities. This process, and the compositions produced, provide significant advantages in the manufacture of pharmaceutical particulate formulations, as well as biomedical, diagnostic, and chromatography particulate compositions, where sensitive macromolecules, such as proteins or DNA, are involved that would be degraded using more rigorous processing conditions or temperatures.

2. Description of Related Art

Conventional particle formation methods by crystallization, solvent evaporation, and filtration are known. Particle size is often reduced through secondary processing such as milling, while particle size may be increased through granulation and spray-coating techniques. Unfortunately, for small nanoparticles and microparticles used for inhaled, nasal, injectable, oral, and topical delivery, the resulting particles are highly charged and very cohesive, reducing their manufacturability and delivery efficiency and subsequent therapeutic efficacy. Therefore, what is needed are improved methods for preparing particles that do not suffer these limitations, and that are useful in preparing particles with distinct particle sizes and surface properties to obtain a superior final product.

There has been substantial effort in the last decade to produce drug particles from 100 nanometers to a few microns because of their improved dissolution properties (especially with insoluble drugs) and ability to be absorbed more efficiently. Drug particles, such as nanoparticles and microparticles, are usually formed either by size reduction (dry or wet milling) (Liversidge, Cundy et al. 1992), spray-drying, precipitation upon addition of a non-solvent, gelling the drug/polymer upon changing the pH or addition of a precipitating ions (salts) (Woiszwillo, Brown et al. 1999), or complexing a drug with a polymer of an opposite charge. For polymeric nanospheres or microspheres formed by emulsion techniques, the interior core of the particle is gelled and hardened, followed by collection through filtration or centrifugation. Microencapsulated particles include small particles with a drug dispersed in a polymer, or covered with a thin layer of coating material surrounding a nanoparticle or microparticle core. Microencapsulated drug particles may include a drug core with a coating on the surface that is made from a polymer or other material with the desired surface properties, which may improve the adhesion properties to a biological surface, sustain the release of the drug in a biological system or protect a drug from degradation under low pH or enzymatic cleavage (such as in the stomach). These systems, however, tend to be characterized by poor reproducibility and scalability in manufacturing, low encapsulation efficiencies (for microencapsulated particles), damage/denaturation of the drug when it is a macromolecule due to the use of organic solvents and/or spray-drying (Cleland and Jones 1996; Cleland, Mac et al. 1997), and poor shelf-life (Niemi, Turakka et al. 1990; Bartus, Tracy et al. 1998; Na, Stevens et al. 1999; Williams and Hu 2000; Suzuki, Ogawa et al. 2001). An example of a drug particle microencapsulation process is also described in U.S. Pat. No. 6,406,745, which may be used to microencapsulate drug particles efficiently without the use of solvents or high temperatures that may damage the drug molecule or activity (Talton 2002).

Final dosage forms incorporating drug particle compositions, such as a tablet or a solution for injection, typically contain bulking agents and/or surface stabilizers that may be chemically or physically attached on the surface, or more simply physically mixed, to disperse effectively. Oral tablets and capsules, as well as inhaled dry-powders, typically incorporate at least one pharmaceutically acceptable water-soluble or water-dispersible excipient. Common agents are known in the art as carriers, dispersants, or generally excipients, which require additional mixing to obtain biological activity upon storage and administration of a final dosage form. Because of the inherently high electrostatic forces present in nanoparticles and microparticles, direct mixing with carrier particles, such as in dry-powder inhaled formulations, may be inefficient and result in low quality final products. For this reason, manufacturing of nanometer and micrometer size drug particles that include excipients before the bulk mixing phase to improve the dispersion properties are of great interest to produce an improved final product.

Several groups have also explored the use of single-component drug particle systems with bioadhesive polymers to improve particle or drug adhesion to cell membranes and enhance absorption. A variety of materials have been shown to be successful including celluloses, hydrogel polymers, polycarbophils, polyanhydrides, polyacrylic acids, alginates, gelatins, gums, and pectin. Adhesion may be affected by physical or mechanical bonds, secondary chemical bonds, and/or primary, ionic or covalent bonds, which can improve the adhesion of bulk dosage forms or single particles. Reports have also shown that the adhesiveness of polymers to mucin/epithelial surfaces may be improved with anionic polymers with a high charge density. In U.S. Pat. No. 6,428,814, bioadhesive nanoparticles consisting of active cores coated with cationic surface stabilizers are described, which suggest increased adhesion to mucosal surfaces, such as the gastrointestinal (GI) tract, for systemic drug delivery (Bosch, Cooper et al. 2002). In U.S. Pat. No. 6,235,313, bioadhesive polymers were identified that were used as matrices during particle formation, producing particle surfaces that retain the bioadhesive properties of the polymer while encapsulating drugs within the particle (Mathiowitz, Chickering et al. 2001). Use of metal ions on the particle surface has also been used to enhance the bioadhesive properties of a polymer to enhance the adhesion to a tissue surface, such as a mucosal membrane (Jacob and Mathiowitz 2002). Metal compounds which enhance the bioadhesive properties of a polymer, as well as aid in the incorporation/precipitation of proteins during microencapsulation, typically include metal oxides and hydroxides, including oxides of calcium, iron, copper and zinc. Sustained-release profiles can be achieved after oral administration of drugs, such as proteins, by inclusion of metal-salts as complexing agents, as well as polymer degradation modifiers and stabilizers, particularly zinc (Jacob and Mathiowitz 2002).

Delivery of discrete nanoparticles and microparticles have been investigated for inhalation, nasal, topical, ocular, buccal, and injectable delivery. Pulmonary delivery of low molecular-weight drugs, peptides/proteins, and gene-therapy agents for local or systemic therapies presents unique formulation challenges. Efficient and reproducible drug deposition to central sections of the lung, such as glucocorticoids for asthma therapies, and peripheral sections of the lung for systemic delivery, such as insulin for patients with diabetes, is difficult because of limitations involved in aerosolization, stability, and clearance of micron-sized liquid droplets and powders. Currently available delivery systems for the inhalation of drugs include metered-dose inhalers (MDI's), dry-powder inhalers (DPI's), and nebulizers. Inhaled delivery of small molecule drugs including beta-agonists, such as albuterol, and glucocorticoids, such as budesonide and fluticasone propionate, have been used clinically for decades where small portions (20-200 µg) of the packaged dose are deposited in the desired portions of the lung (typically 5-10%). New non-invasive inhaled therapies being developed, such as peptides and proteins intended for systemic delivery, have distinctive physicochemical properties that further complicate efficient delivery, as well as may require large 'lung-doses' in the order of 2-20 mg, i.e. insulin. Dry-powder formulations of macromolecules are of particular interest for inhaled therapies since their stability is higher in the dry-state. Unfortunately, current formulations and inhalers are inefficient with fine particle doses of 5-20% of total emitted dose and high dose-to-dose variability. Coupled with regulatory requirements that inhaler systems meter and aerosolize micronized (usually <5 µm) powders reproducibly and several therapies have narrow therapeutic windows, improved inhaler devices and powder processing techniques are necessary to efficiently deliver therapeutics through the pulmonary route.

Spray-drying has been recognized as a viable alternative for the production of drug particles of controlled size in a one-step process. Generally, spray-dried particles are spherical and often hollow, resulting in a powder with a low bulk density in comparison to the starting material. The major drawback of the spray-drying process is that, due to the rapid drying of liquid droplets, metastable, high-energy amorphous forms of therapeutic compounds that may crystallize over time (amorphous to crystalline transition) are formed that influence product performance. Improved aerosol efficiency can also be achieved by co-spray drying with excipients such as salts, poly-peptides, carbohydrates such as lactose, mannitol, or trehalose, and lipids such as lecithin or phosphatidyl choline (Patton, Foster et al. 1999; Foster, Kuo et al. 2001). Particles of insulin, $\alpha$-1-antitrypsin, and $\beta$-interferon have all been successfully prepared by co-spray drying with excipients. Unfortunately, typical spray-drying techniques require high inlet temperatures to obtain unagglomerated powders with low moisture content, which deactivates portions (10-80%) of the final product and have limited shelf-life (Adler and Lee 1999; Stahl, Claesson et al. 2002). Co-spray drying with carbohydrates (glass stabilization), such as trehalose, also improves the shelf-life stability of the peptide or protein. Sugars have also been used extensively to improve stability of lyophilized protein formulations for injection. These formulations in the "glass state" remain stable for long periods of time when stored well below the glass transition temperature, Tg. Unfortunately, for pulmonary applications where delivery of a maximum powder dose is limited, the use of significant quantities of additional excipient required to achieve stable particles limits the amount of the therapeutic dose achievable.

Drug particles have also been prepared using Super Critical Fluid (SCF) condensation methods, which take advantage of phase transitions of mixtures above a critical temperature and pressure (Palakodaty and York 1999). In the SCF region, these mixtures exist as a single phase and possess the solvent power of liquids together with the mass transfer properties of gases. Carbon dioxide is the most commonly used SCF because it is non-toxic, non-flammable, inexpensive, and has a low critical temperature that allows operation under ambient conditions. Similar to spray-drying, SCF processing may involve aerosolization and rapid dispersion/extraction of the organic solvent. Temperature and pressure regulation, together with precise metering of flow rates, provides control over mixing, nucleation and particle formation (Hanna and York 2000). Water-soluble compounds, such as peptides and proteins, are more challenging for SCF processing as they are insoluble in organic solvents. Similar to spray-drying, protein stabilization using carbohydrates is required in order to retain activity. The resulting drug particles are highly crystalline and particle-size is controlled by regulating the fluid dynamic interactions, but production rate is typically slow and requires specialized equipment and experience.

Sonication of liquids may be used to produce high shear forces and cavitation at high frequencies (Suslick, Doktycz et al. 1990). Ultrasonic frequencies (20-22 kHz) are typically used to disrupt cell membranes to analyze cell components, in addition to cleaving DNA (Elsner and Lindblad 1989). Sonication has also been used to form microbubbles for imaging agents (David, J. et al. 1990) using viscous aqueous solutions of sorbitol or dextrose, as well as heat-sensitive proteins such as albumin, at lower frequencies (5 to 10 kHz). While these techniques illustrate the formation of particles from solution at high ultrasonic frequencies, the nature of these processes involve cavitation and formation of microbubbles at hundreds of degrees or higher, which denature the solutes, such as albumin, into an insoluble spherical bubble. While this technique is advantageous for the production of gas-filled bubbles for enhancing ultrasound imaging of vascular systems, the application of these conditions for forming therapeutic drug particle systems is limited.

Ultrasonic frequencies (20 kHz) have also been used to form polymeric strands with high crystallinity at room temperature (Kirby 1998). In an earlier related technique, varying the frequency range from 80 to 2,000 Hz for short periods of time was also found to crystallize polymer fibers from solution (Keller and Jenkins 1978). The formed polymer mass with high surface area was then removed and air-dried for further processing. None of these techniques, though, anticipate the use of low-frequency sonication (LFS) in the range of 1 to 1,000 hertz, in combination with vacuum drying, to form drug particles of controlled composition and particle size in a one-step process.

III. SUMMARY OF THE INVENTION

A. Features and Advantages of the Invention

The present invention overcomes these and other inherent deficiencies in existing methods by providing novel particle forming methods for use in preparing improved pharmaceutical products. The described processes involve forming particles, which may include drugs, in a solution, changing the bulk or surface properties of a particle, and/or microencapsulating particles, and compositions produced thereby. The process utilizes mechanical agitation, more specifically low-frequency sonication, under controlled conditions, which provide mild shear forces during precipitation to control the particle growth and mixing properties. Particle size control from <200 nanometers to greater than one millimeter is shown, which has not been described using other known systems. Drug particles may be (1) formed in a solution to obtain a particle suspension and then collected, (2) dried a wet powder slurry or suspension, and/or (3) sonicated dry to anneal/condition the structure of the particle or particle surface. In addition, the process can be used to microencapsulate particles by suspending the drug particles in a solution including a coating material (such as a biodegradable polymer) and evaporating the solution under controlled process conditions. The drug particle compositions produced thereby possess improved properties including, but not limited to, improved flow and dispersibility, controlled bioadhesion, stability, resistance to moisture, dissolution/release profiles, and/or bioavailabilities. This process, and the compositions produced, provide significant advantages in the manufacture of pharmaceutical particulate formulations, as well as biomedical, diagnostic, and chromatography particulate compositions, where sensitive macromolecules, such as proteins or DNA, are involved that would be degraded using more rigorous processing conditions or temperatures. The processes are not limited to those for making drug particles, and they may be extended to processes for making particles that do not include drugs.

B. Summary of the Invention

The present invention provides methods of forming drug particles, comprising: providing a drug in an initial solution; agitating said drug in said initial solution using low-frequency sonication; evaporating a portion of the initial solution; and collecting said drug particles. The drug particles may have diameters from less than about 100 nanometers to greater than about 1 millimeter. The forming may occur under low-frequency sonication at about 1 hertz to about 1,000 hertz. The low-frequency sonication may be constant, intermittent, or cycled.

The drug may comprise at least one water-soluble or water-insoluble compound, amino acid, peptide, protein, sugar, lipid, DNA, and/or polymer. The initial solution may comprise at least one from the list of water, an alcohol, or an organic solvent. The agitating may include low-frequency sonication, stirring, and/or inclusion of beads. The forming may occur at a pressure of about 1 Torr or higher, including about 200 to about 400 Torr. The forming may occur at a temperature of about 0 degrees Celsius or higher, including about 10 to about 60 degrees Celsius.

The forming may comprise adding a second solution. The second solution may include water, an alcohol, organic solvent, and/or a precipitation agent. The precipitation agent may include a metal salt, lipid, and/or polymer. In another embodiment, the second solution incorporating a drug is added to the initial solution under low-frequency sonication to precipitate drug particles.

In other embodiments, the present invention includes methods of forming drug particles having a diameter of less than about 100 nanometers to greater than about 1 millimeter, the method comprising: providing a drug in an initial solution; agitating said drug in said initial solution using low-frequency sonication, stirring, and inclusion of beads; adding a second solution; evaporating a portion of the initial and/or second solution; and collecting said drug particles.

In other embodiments, the present invention includes methods of forming drug particles having a diameter of less than about 100 nanometers to greater than about 1 millimeter, comprising: providing an initial solution; agitating said initial solution using low-frequency sonication, stirring, and inclusion of beads; adding a drug in a second solution; evaporating a portion of the initial and/or second solution; and collecting said drug particles.

In other embodiments, the present invention includes a drug particle forming apparatus comprising: a chamber for containing a drug in an initial solution; a low-frequency vibration source near the bottom of said chamber for agitating said drug in said initial solution; at least one input port into said chamber for adding a second solution and/or a gas; at least one output port near the top of said chamber for providing a vacuum and evaporating a portion of the initial and/or second solution; at least one output port into said chamber for collecting said drug particles.

The present invention also provides drug particles formed according to these methods.

IV. BRIEF DESCRIPTION OF THE DRAWINGS

The drawings form part of the present specification and are included to further demonstrate certain aspects of the present invention. The invention may be better understood by reference to one or more of these drawings in combination with the detailed description of specific embodiments presented herein.

FIG. 1 is a block diagram of the microparticle forming/modification process.

FIG. 2 is a general illustration of the particle forming/modification/coating apparatus.

FIG. 3 is a general illustration of the particle forming/modification/coating apparatus with additional heating.

FIG. 4 is a general illustration of the particle forming/modification/coating apparatus with additional stirring.

FIG. 5 is a general illustration of the particle forming/modification/coating apparatus with additional motion-joined (MOJO) beads.

FIG. 6 shows SEM images of A) albuterol sulfate particles (5,000× magnification) and B) promethazine particles (5,000× magnification).

FIG. 7 shows an A) SEM image of albumin+dynorphin particles (5,000× magnification) and B) digital microscope image of lysozyme crystals (60× magnification).

V. DETAILED DESCRIPTION OF THE INVENTION

The invention is directed to methods of forming/modifying particulate materials, and the particulate materials produced thereby. Particulate materials, also designated as "drug particles," to be produced in accordance with this invention include those in which small nanometer to micrometer size particles are desirable. Such drug particles compositions include, but are not limited to, drugs or pharmaceuticals for human or animal use, cosmetics, pesticides, herbicides, fungicides, paints and pigments, as well as inert particles for which a small particle is desirable. Examples include nanoparticles and microparticle forms of antigens, nucleic acids, proteins, or even pharmaceuticals. The possibilities and combinations are numerous.

A. Methods for Forming and/or Modifying Drug Particles

The present invention provides an improved method and apparatus for preparing drug particles. Controlled particle size, shape, and surface properties, as well as high yield of stable drug particles, are important aspects of the described process. The present invention utilizes the discovery that the formation of particles under low-frequency sonication (LFS), generally about 1 to about 1,000 hertz, provides more homogeneity than typical propeller mixers or homogenizers, but does not produce cavitation which may damage some fragile drug molecules, such as proteins and DNA. The size of the resulting particles is primarily controlled by the intensity of the low-frequency sonication of the vessel transferred to the solution, and other controlled conditions during the particle forming/modification step of the process of the present invention. It has been found that particle size may be limited to less than about a few microns under more intense LFS conditions, while crystals of about several hundred microns are possible under less intense LFS conditions, described in the present invention. Agitation is produced through mechanical vibration at low frequencies, i.e. LFS, of a vessel containing a solution, suspension, or dry powder. Additional bulk agitation/mixing may be produced through rocking the vessel, stirring, or adding beads to the vessel. The inventors of the present invention have unexpectedly found that stable drug particles of controlled particle size and structure may be formed rapidly (typically <1-24 hours) using LFS at low temperature (typically 5-50° C.) under mild vacuum (typically 200-760 Torr). In addition, a mild vacuum, a dry gas (room-air, nitrogen, helium, etc.), solvent-rich vapor (water, alcohol, organic, etc.), or additional solution or powder may be introduced which may further modify/anneal the entire drug particle and/or the surface of the drug particle. The LFS applied to a solution or suspension has been found to increase the evaporation rate of liquids, as well as fluidize particles to modify/anneal the bulk and/or surface properties, under controlled conditions. In addition, improved mixing/agitation may be produced through stirring using an impellor, as well as addition of motion-joined (MOJO) beads, to transfer the sonication energy into the bulk fluid and/or further provide attrition during the process. The principle of motion-joined (MOJO) beads is introduced which, contrary to typical ball-milling of powders, MOJO beads are present during the particle forming process that vibrate according to the LFS level and frequency, transferring further the sonication energy into the bulk solution, and limit particle size and further modifying the surface morphology.

In general, the setup includes a vessel with pressure and temperature control that is mechanically agitated by LFS applied to the bottom to promote drug particle formation/modification/coating under controlled conditions. A solution, suspension, or powder is placed in a vessel fitted with a top with ports and placed onto a LFS platform. The gas in and vacuum out ports are opened and the temperature is set to the desired process temperature. The LFS is then engaged which provides the main agitation process for the process. The LFS may be at a constant frequency and amplitude, intermittent, or cycled (micropulses) according to a programmed set of conditions over time. Additional parameters to produce drug particles with desired properties include additional agitation/stirring, pressure and temperature control, gas/vapor/liquid/powder inputs, as well as run-time at various stages.

Figure 1:
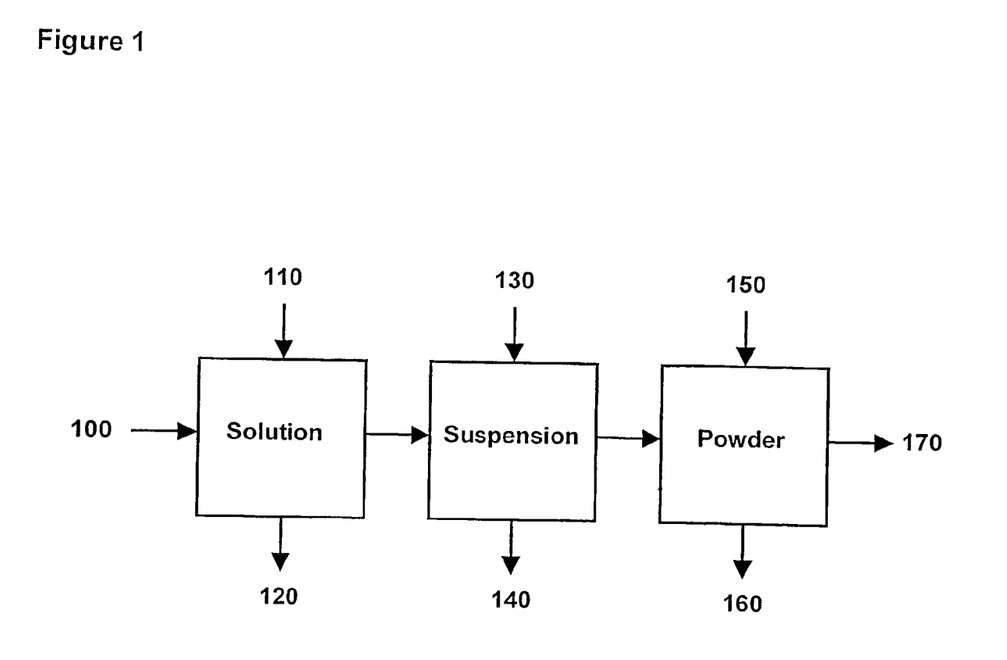

The block diagram shown in FIG. 1 of forming/modifying drug particles displays the general process which involves a starting solution, a suspension, and a drug particle powder and the various inputs and outputs at each stage. The original start solution 100 is placed in the vessel and inputs 110 such as room-air/dry-gas or complexing agent in a second solution is added after the initial temperature, pressure, and LFS conditions are reached. Outputs 120 at this stage would include a vacuum source or solvent vapor collection. In the suspension stage, after drug particles form or if drug particles in a suspension is the initial state, inputs 130 can include room-air/dry-gas or a second solution containing a polymer for microencapsulation in a similar/miscible solvent or non-solvent. The outputs 140 can include a vacuum source, solvent collection, or removal of the suspension for additional processing, such as filtration and drying. When the suspension is nearly dry, final inputs 150 can include room-air, dry-gas, a conditioning vapor, and/or wet or dry excipients for physical mixing/granulation. Final outputs 160 can include a vacuum source or solvent collector. At the end of the process the final drug particle pharmaceutical powder product 170 is then removed. At the different stages, temperature, pressure, LFS, additional agitation, product samples, or process monitoring may be involved. Each of these unit operations will be described in greater detail below.

B. Apparatus for Forming and/or Modifying Particles

Figure 2:
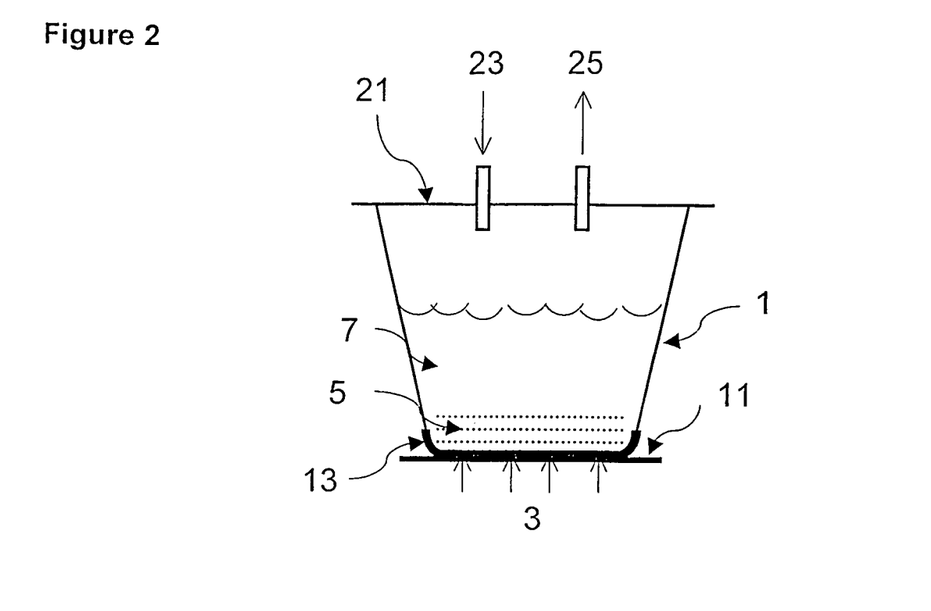

FIGS. 2 through 5 show examples of particular methods. The apparatus shown in FIG. 2 depicts one embodiment of the drug particle forming/modification/coating apparatus. The vessel 1 with the bottom in contact with the LFS source 3 encloses a solution 7 and/or drug particles 5. The LFS may be produced using a oscillating magnet (fixed at top to LFS baseplate), a motor piston imparting single axis motion, or similar device. An LFS baseplate 11 may include an external heating source 13 that controls the temperature of the process. In addition, a gas-tight cover 21 is placed on top with an input port 23 and an output port 25.

Figure 3:
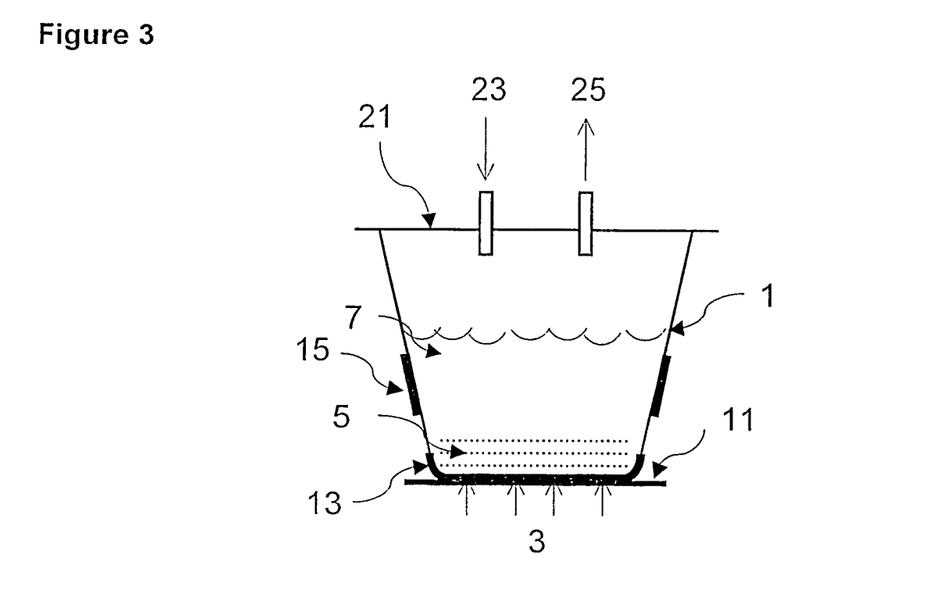

The apparatus shown in FIG. 3 depicts a similar drug particle forming/modification/coating apparatus to FIG. 2 with additional heating 15. The additional heat source, covering a substantial portion of the outside surface of the vessel, may be used to increase the solvent drying rate for larger drug particle batches, such as with a large reactor vessel (>100 liters).

Figure 4:
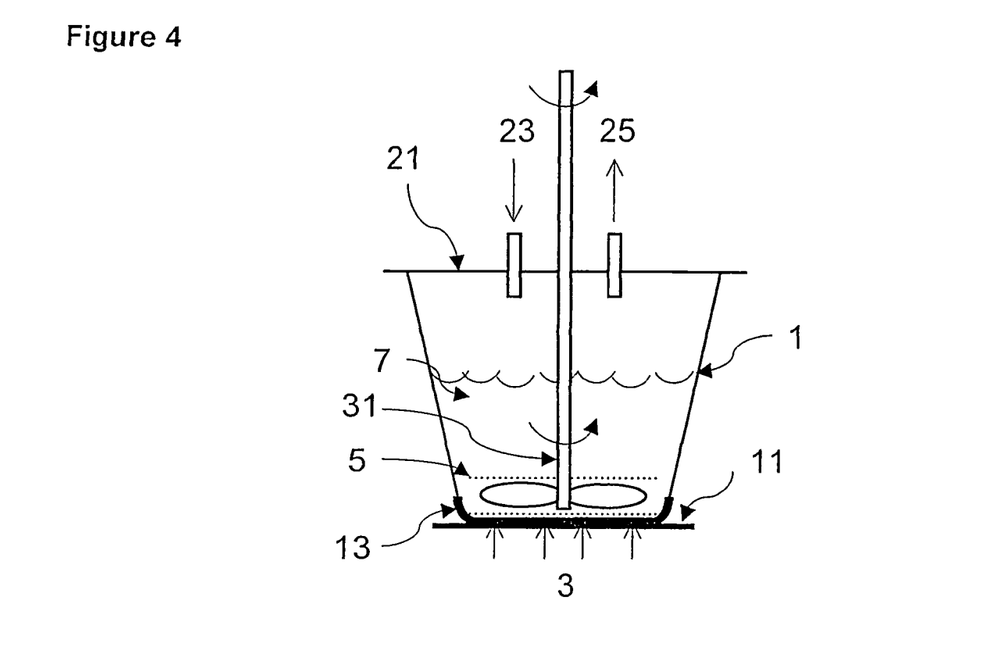

The apparatus shown in FIG. 4 depicts a similar drug particle forming/modification/coating apparatus to FIG. 2 with additional stirring 31. The stirring paddle or blade may be used to impart higher shear forces to improve mixing, reduce particle size, or detach drug particles from the vessel.

Figure 5:
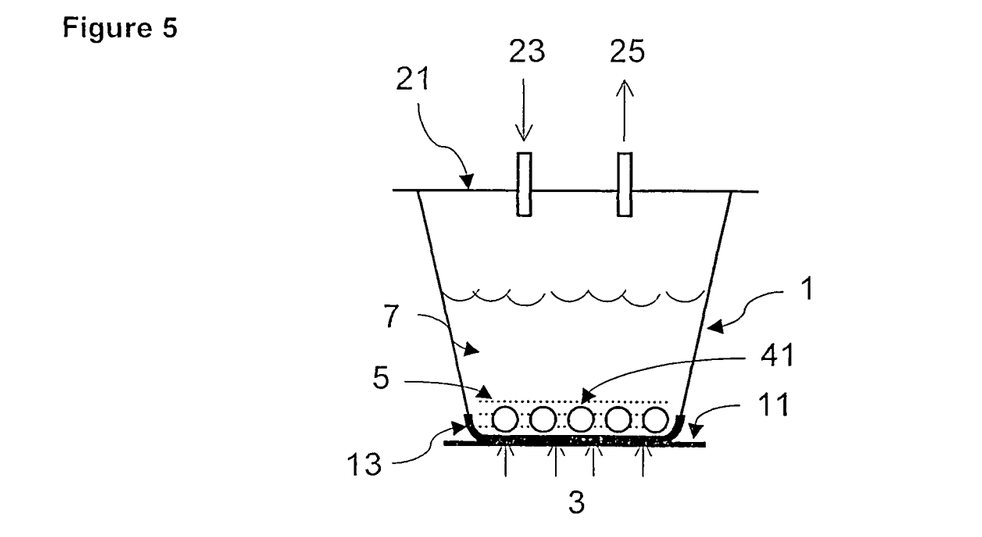

The apparatus shown in FIG. 5 depicts a similar drug particle forming/modification/coating apparatus to FIG. 2 with additional mixing/attrition due to the presence of MOJO beads 41. The MOJO beads, which move according to agitation/vibration transferred from the bottom of the vessel, also may be used to improve mixing, reduce particle size, smooth drug particle morphology, or detach microparticles from the vessel.

While various embodiments of the present invention have been described above, it should be understood that they have been presented by way of example only, and not limitation. The present invention is not limited to the preparation of drug particles, nor is it limited to a particular drug, solution, or final product, nor is the present invention limited to a particular scale or batch size. The present invention is not limited to any particular type or design of vessel. Thus, the breadth and scope of the present invention should not be limited by any of the above-described exemplary embodiments, but should be defined only in accordance with the following claims and their equivalents.

C. Drug Particle Compositions

The drug particle forming/modification techniques described herein, and the compositions derived therefrom, are applicable to a wide variety of compositions, including, but not limited to, pharmaceutical compositions for human or veterinary use, biotechnology applications, herbicides, or pesticides. Pharmaceutical compositions include organic and inorganic active compounds, including biologically active peptides, proteins, and nucleic acids. Pharmaceutical compositions of the invention may be delivered by inhalation through the respiratory tract, as well as, orally, parenterally, or transdermally. In the embodiment of an implant, or other slow release formulation, such compositions may be manually placed into a body. In addition, microencapsulation may be added to the drug particle surface so the drug core may be carried to a specific tissue. Methods of delivery of such compositions are well known in the art, and are described, for example, in Modern Pharmaceutics, Second Edition, edited by Gilbert S. Banker and Christopher T Rhodes, the entire contents of which is hereby incorporated by reference.

In one embodiment, an oral drug particle is formulated with the present invention. Exemplary pharmaceuticals that would benefit from such drug particle formulations include drugs used in controlled or targeted release, taste-masking, or surface modification prior to tableting or capsule filling.

In another embodiment, a pulmonary dry-powder formulation is prepared incorporating drug particles and excipients of the present invention. Exemplary pulmonary drugs that could be used include glucocorticoids and other localized asthma drugs, as well as drugs and bioactive peptides and proteins for systemic delivery, such as insulin.

Topical drugs that can be used include localized antibiotics, antifungals, and anti-inflammatories. Parenteral drugs that can be used include many currently used suspensions and preparations for sustained or localized release, or simply to reduce hydration and improve shelf-life of protein powders.

In illustrative embodiments, the drug particles range in size from about 10 or about 20 nm in average diameter up to and including about 1 or about 2 mm in diameter. More preferably the drug particles may be range in size from about 100 or about 200 nm in diameter up to and including about 100 to about 200 microns in diameter. In other embodiments, drug particles may range in size from about 500 or about 600 nm in diameter up to and including about 10 or about 15 microns in diameter. By modifying the particular parameters of the drug particle forming/modifying process, particles of slightly larger or smaller average diameter particle sizes, may be obtained.

D. Examples

The following examples are included to demonstrate representative embodiments of the invention. It should be appreciated by those of skill in the art that the techniques disclosed in the examples which follow represent techniques discovered by the inventors to function well in the practice of the invention, and thus can be considered to constitute relevant examples for its practice. However, those of skill in the art should, in light of the present disclosure, appreciate that many changes can be made in the specific embodiments which are disclosed and still obtain a like or similar result without departing from the spirit and scope of the invention.

Example 1

A solution of lactose (10 g) and leucine (0.2 g) in water (100 ml) was agitated in a stainless steel bowl using low frequency sonication (60 hertz, 70% max) with one MOJO bead (1 cm ceramic marble) at a temperature of 25 degrees Celsius (no heating) at 300 to 400 Torr for 24 hours. A white powder was obtained with a yield of 9.2 g, containing particles with a diameter less than 10 microns. The particles appeared crystalline having little amorphous character. The particles obtained could be used as a carrier for use in a dry powder inhaler or oral capsule formulation.

Example 2

A solution of lactose (10 g) and PEG 8,000 (0.2 g) in water (100 ml) was agitated in a stainless steel bowl using low frequency sonication (60 hertz, 70% max) with five MOJO beads (1 cm ceramic marbles) at a temperature of 40 degrees Celsius (low heat) at 300 to 400 Torr for 4 hours. A white powder was obtained with a yield of 9.6 g, containing particles with a diameter from 1 to 10 microns. The particles appeared slightly amorphous in character. The particles obtained could be used as a carrier for use in a dry powder inhaler or oral capsule formulation.

Example 3

Figure 6:
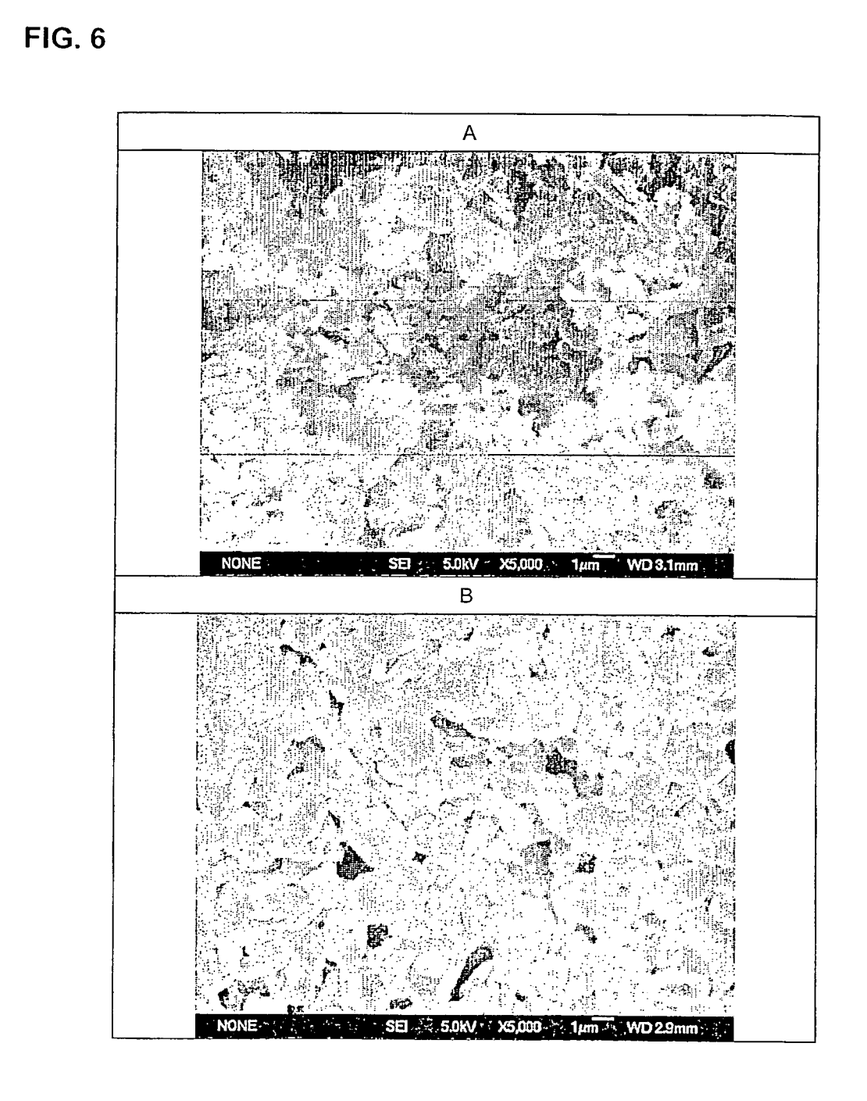

A solution of albuterol sulfate (10 g) and leucine (0.2 g) in water (100 ml) was agitated in a stainless steel bowl using low frequency sonication (60 hertz, 70% max) with five MOJO beads (1 cm ceramic marbles) at a temperature of 30 degrees Celsius (low heat) at 300 to 400 Torr for 4 hours. A white powder was obtained with a yield of 8.0 g, containing particles with a diameter from 1 to 5 microns. The particles are shown in FIG. 6A and appeared highly crystalline in character. The particles obtained could be used in a dry powder inhaler for asthma therapy.

Example 4

A solution of promethazine (10 g) in water (100 ml) was agitated in a stainless steel bowl using low frequency sonication (60 hertz, 70% max) with five MOJO beads (1 cm ceramic marbles) at a temperature of 30 degrees Celsius (low heat) at 300 to 400 Torr for 4 hours. A white powder was obtained with a yield of 8.0 g, containing particles with a diameter from 1 to 5 microns. The particles are shown in FIG. 6B and appeared highly crystalline in character. The particles obtained could be used in a dry powder inhaler for motion-sickness.

Example 5

A solution of sumatriptan succinate (1 g) in water (100 ml) was agitated in a stainless steel bowl using low frequency sonication (60 hertz, 70% max) with five MOJO beads (1 cm ceramic marbles) at a temperature of 30 degrees Celsius (low heat) at 300 to 400 Torr for 4 hours. A white powder was obtained with a yield of 9.0 g, containing particles with a diameter from 1 to 5 microns. The particles appeared highly crystalline in character. The particles obtained could be used in a dry powder inhaler or nasal inhaler for migraine therapy.

Example 6

A solution of ceftriaxone (5 g) in water (50 ml) was agitated in a stainless steel bowl using low frequency sonication (60 hertz, 60% max) with three MOJO beads (1 cm teflon coated metal bearings) and stirred with a 4 inch rotor at 1 RPM. The temperature was 25 degrees Celsius (no heat). Ethanol was added (50 ml) to precipitate the drug and allowed to continue at 300 to 400 Torr for 30 minutes. The suspension was filtered and a white powder was obtained with a yield of 4.2 g, containing particles with a diameter from 1 to 5 microns. The particles appeared highly amorphous in character and dissolved quickly upon addition of water. The particles obtained could be used in an IV infusion (after reconstitution) or an oral formulation for treatment of an infectious pathogen.

Example 7

A solution of poly(lactic-co-glycolic acid) (100 mg) in chloroform (50 ml) was prepared, then ceftriaxone microparticles (2 g) from Example 7 were added to form a suspension. The suspension was agitated in a stainless steel bowl using low frequency sonication (60 hertz, 60% max) with three MOJO beads (1 cm teflon coated metal bearings) and stirred with a 4 inch rotor at 1 RPM. The temperature was 25 degrees Celsius (no heat). Ethanol was added (50 ml) to precipitate the PLGA onto the ceftriaxone microparticles and allowed to continue at 300 to 400 Torr for 30 minutes. The suspension was filtered and lyophilized, a white powder was obtained with a yield of 1.8 g, containing particles with a diameter from 1 to 5 microns. The particles appeared slightly clumped and dissolved slowly upon addition of water. The particles obtained could be used in a slow-release oral formulation for treatment of an infectious pathogen.

Example 8

A solution of lidocaine HCl (400 mg) in water (100 ml) was agitated in a stainless steel bowl using low frequency sonication (60 hertz, 60% max) with three MOJO beads (1 cm teflon coated metal bearings) and stirred with a 4 inch rotor at 1 RPM. The temperature was 25 degrees Celsius (no heat). Capric acid (400 mg) in ethanol (10 ml) was added, the pH was increased with NaOH added dropwise until a precipitate formed, and the entire process allowed to continue at 300 to 400 Torr for 30 minutes. The suspension was filtered and a white powder was obtained with a yield of 250 mg, containing particles with a diameter from 1 to 5 microns. The particles appeared highly amorphous in character and dispersed completely (but did not dissolve) upon addition of water. The particles obtained could be used in a topical application, or similar modification of other poorly absorbed bases could be formed as salts of lipids for permeation enhancement.

Example 9

A solution of Carbomer 940 (1 g) in water (400 ml) was agitated in a stainless steel bowl using low frequency sonication (60 hertz, 60% max) with three MOJO beads (1 cm teflon coated metal bearings) and stirred with a 4 inch rotor at 1 RPM. The temperature was 25 degrees Celsius (no heat). A second solution of progesterone (2 g) in ethanol was added (50 ml) and the progesterone precipitated and allowed to continue at 300 to 400 Torr for 1 hour. The suspension was centrifuged and a White powder was obtained with a yield of 1.2 g, containing particles with a diameter from 1 to 5 microns. The particles appeared highly crystalline in character and dissolved quickly upon addition of water. The particles obtained could be used in a topical cream or an oral formulation for treatment of hormone deficiency.

Example 10

A solution of insulin (200 mg) in water (50 ml) was adjusted to pH <3 with HCl and then agitated in a stainless steel bowl using low frequency sonication (60 hertz, 70% max) with five MOJO beads (1 cm ceramic marbles) at a temperature of 30 degrees Celsius (low heat). The pH was increased with NaOH added dropwise until a precipitate formed and allowed to continue at 300 to 400 Torr for 1 hour. The suspension was filtered and a white powder was obtained with a yield of 50 mg, containing particles with a diameter from 1 to 5 microns. The particles appeared highly amorphous in character and dissolved quickly upon addition of water. The particles obtained could be used in a dry powder inhaler for diabetes.

Example 11

A solution of insulin (200 mg) in water (50 ml) was adjusted to pH <3 with HCl and then agitated in a stainless steel bowl using low frequency sonication (60 hertz, 70% max) with five MOJO beads (1 cm ceramic marbles) at a temperature of 30 degrees Celsius (low heat). Zinc acetate (10 mg) was added and the pH was increased with NaOH added dropwise until a precipitate formed and allowed to continue at 300 to 400 Torr for 1 hour. The suspension was filtered and a white powder was obtained with a yield of 80 mg, containing particles with a diameter from <1 to 5 microns. The particles appeared highly amorphous in character and dissolved quickly upon addition of water. The particles obtained could be used in a dry powder inhaler or an oral capsule formulation for diabetes.

Example 12

Figure 7:
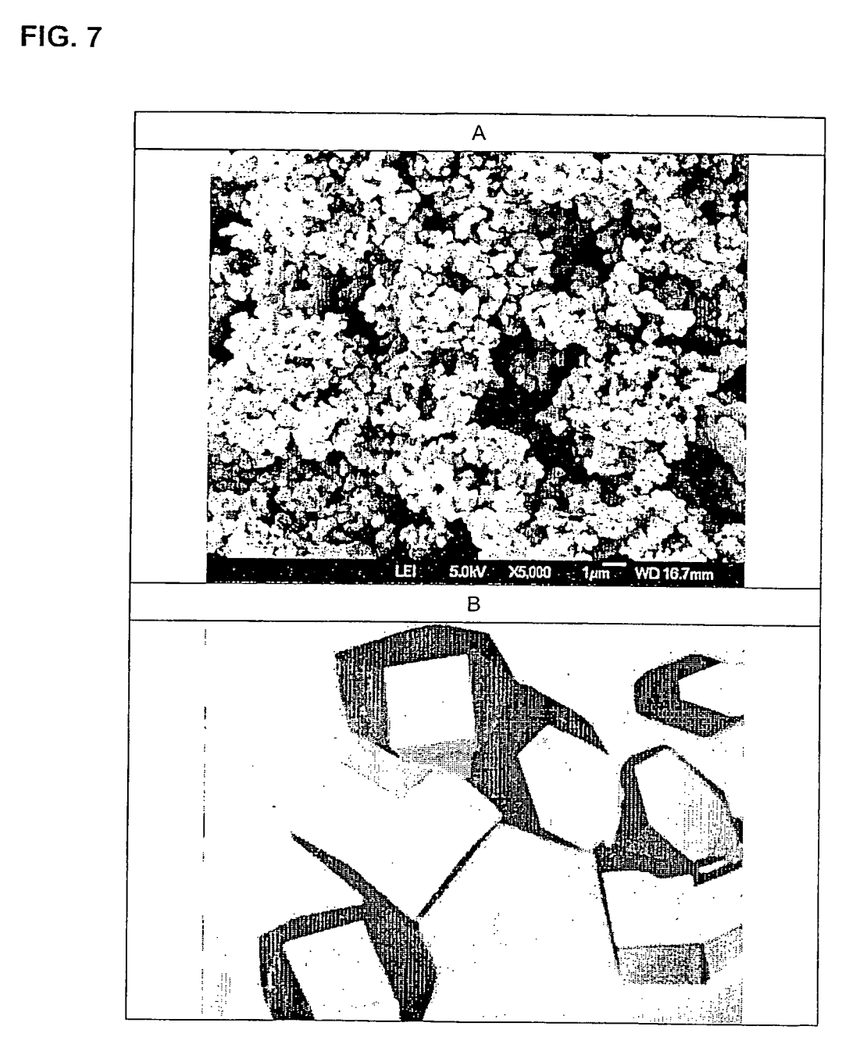

A solution of bovine serum albumin (450 mg) and dynorphin A1-13 amide peptide (50 mg) in water (50 ml) was adjusted with sodium acetate (10 mM) and then agitated in a stainless steel bowl using low frequency sonication (60 hertz, 70% max) with five MOJO beads (1 cm ceramic marbles) at a temperature of 30 degrees Celsius (low heat). Zinc acetate (10 mg) was added dropwise until a precipitate formed and allowed to continue at 300 to 400 Torr for 1 hour. The suspension was filtered and a white powder was obtained with a yield of 200 mg, containing particles with a diameter of 400 nm to <1 micron. The particles are shown in FIG. 7A and appeared very small in size and dissolved slowly (>4 days) upon mixing with phosphate buffer. The particles obtained could be used in a dry powder inhaler for treatment of morphine addiction. Other proteins, such as sub-units for vaccine, could also be potentially complexed with albumin for inhalation, nasal, or oral delivery, as well as by injection after reconstitution.

Example 13

A solution of modified tomato plasmid DNA (5 mg) in Tris buffer (50 ml) was agitated in a stainless steel bowl using low frequency sonication (60 hertz, 60% max) at a temperature of 25 degrees Celsius (no heat). PEI (1 mg) and PEG 8,000 (9 mg) in Tris buffer (50 ml) was added and a precipitate formed and allowed to continue at 300 to 400 Torr for 10 minutes. The suspension was added directly to tomato leaf protoplasts for transfection. The resulting solution was analyzed under an optical microscope and very small (<1 micron) particles were observed. Similar DNA/RNA nanoparticle suspensions could be obtained for gene transfer of any relevant biological system, i.e. cells, plants, humans, etc.

Example 14

Solutions of lysozyme (HEWL, 50 mg/ml), glycerol (0.5%), PEG 8,000 (0.5%), and NaCl (1-5%) in water (0.2 ml) were placed in a 96 well plate and then agitated using low frequency sonication (60 hertz, 30% max) at a temperature of 30 degrees Celsius (low heat). The process was allowed to continue at 300 to 400 Torr for 8 hours. Crystals formed to 200 microns in half the time as controls without agitation. The crystals are shown in FIG. 7B with a characteristic lysozyme crystal structure. Crystals were characterized using x-ray crystallography and were similar to crystals grown without agitation for >1 day. Similar conditions could be used to form crystals of different purified proteins and viruses quickly for crystallographic analysis.

VI. CITED DOCUMENTS

Adler, M. and G. Lee (1999). "Stability and surface activity of lactate dehydrogenase in spray-dried trehalose." *J Pharm Sci* 88(2): 199-208.

Bartus, R. T., M. A. Tracy, et al. (1998). "Sustained delivery of proteins for novel therapeutic agents." *Science* 281(5380): 1161-2.

Bosch, H., E. Cooper, et al. (2002). Bioadhesive nanoparticulate compositions having cationic surface stabilizers. *USPTO*. USA, Elan Pharma International Ltd.

Cleland, J. L. and A. J. Jones (1996). "Stable formulations of recombinant human growth hormone and interferon-gamma for microencapsulation in biodegradable microspheres." *Pharm Res* 13(10): 1464-75.

Cleland, J. L., A. Mac, et al. (1997). "The stability of recombinant human growth hormone in poly(lactic-co-glycolic acid) (PLGA) microspheres." *Pharm Res* 14(4): 420-5.

David, C., M. G. J., et al. (1990). Continuous sonication method for preparing protein encapsulated microbubbles. *USPTO*. US, Molecular Biosystems, Inc.

Elsner, H. I. and E. B. Lindblad (1989). "Ultrasonic degradation of DNA." *Dna* 8(10): 697-701.

Foster, L. C., M.-c. Kuo, et al. (2001). Stable glassy state powder formulations. *USPTO*. US, Inhale Therapeutic Systems, Inc.

Hanna, M. and P. York (2000). Method and apparatus for the formation of particles. *USPTO*. US, Bradford Particle Design Limited.

Jacob, J. and E. Mathiowitz (2002). Methods and compositions for enhancing the bioadhesive properties of polymers. *USPTO*. USA, Brown University Research Foundation.

Keller, L. B. and R. K. Jenkins (1978). Process for producing novel polymeric fibers and fiber masses. *USPTO*. US, Hughes Aircraft Company.

Kirby, J. L. (1998). Polymeric strands with high surface area or altered surface properties. *USPTO*. US, Kimberly-Clark Worldwide, Inc.

Liversidge, G., K. Cundy, et al. (1992). Surface modified drug nanoparticles. *USPTO*. USA, Sterling Drug Inc.

Mathiowitz, E., D. Chickering, et al. (2001). Bioadhesive microspheres and their use as drug delivery and imaging systems. *USPTO*. USA, Brown University Research Foundation.

Na, G. C., H. J. Stevens, Jr., et al. (1999). "Physical stability of ethyl diatrizoate nanocrystalline suspension in steam sterilization." *Pharm Res* 16(4): 569-74.

Niemi, L., L. Turakka, et al. (1990). "The influence of ageing on the release of hydrocortisone from o/w creams." *Acta Pharm Nord* 2(1): 21-30.

Palakodaty, S. and P. York (1999). "Phase behavioral effects on particle formation processes using supercritical fluids." *Pharm Res* 16(7): 976-85.

Patton, J., L. Foster, et al. (1999). Methods and compositions for pulmonary delivery of insulin. *USPTO*. US, Inhale Therapeutic Systems.

Stahl, K., M. Claesson, et al. (2002). "The effect of process variables on the degradation and physical properties of spray dried insulin intended for inhalation." *Int J Pharm* 233(1-2): 227-37.

Suslick, K. S., S. J. Doktycz, et al. (1990). "On the origin of sonoluminescence and sonochemistry." *Ultrasonics* 28(5): 280-90.

Suzuki, H., M. Ogawa, et al. (2001). "A nifedipine coground mixture with sodium deoxycholate. II. Dissolution characteristics and stability." *Drug Dev Ind Pharm* 27(9): 951-8.

Talton, J. (2002). Methods for coating particles and particles produced thereby. *USPTO*. USA, Nanosphere, Inc.

Williams, R. O., 3rd and C. Hu (2000). "Moisture uptake and its influence on pressurized metered-dose inhalers." *Pharm Dev Technol* 5(2): 153-62.

Woiszwillo, J., L. Brown, et al. (1999). Macromolecular microparticles and methods of production and use. *USPTO*. USA, Epic Therapeutics, Inc.

What is claimed is:

1. A method of forming drug particles, comprising:

providing a drug dissolved in an initial solution;

sonicating said initial solution of the dissolved drug using low-frequency sonication at a frequency of about 60 hertz to precipitate drug particles from said initial solution, wherein said low-frequency sonication causes said drug particles to precipitate with diameters ranging from about 100 nanometers to about 200 micrometers;

evaporating a portion of the initial solution; and collecting said drug particles.

2. The method of claim 1, wherein the low-frequency sonication is constant, intermittent, or cycled.

3. The method of claim 1, wherein the drug comprises at least one water-soluble or water-insoluble compound, amino acid, peptide, protein, sugar, lipid, DNA, and/or polymer.

4. The method of claim 1, wherein the initial solution comprises at least one selected from the group consisting of water, an alcohol, or an organic solvent.

5. The method of claim 1, wherein the method includes sonicating said initial solution of the dissolved drug using low-frequency sonication and stirring.

6. The method of claim 1, wherein the initial solution further comprises beads.

7. The method of claim 1, wherein the initial solution further comprises beads, and sonicating said initial solution of the dissolved drug further includes stirring.

8. The method of claim 1, wherein the method occurs at a pressure of about 1 Torr or higher.

9. The method of claim 8, wherein the method occurs at a pressure of about 200 to about 400 Torr.

10. The method of claim 1, wherein the method occurs at a temperature of about 0 degrees Celsius or higher.

11. The method of claim 1, wherein the method occurs at a temperature of about 10 to about 60 degrees Celsius.

12. The method of claim 1, further comprising adding a second solution while sonicating said initial solution.

13. The method of claim 12, wherein said second solution comprises at least one selected from the group consisting of water, an alcohol, organic solvent, and/or a precipitation agent.

14. The method of claim 13, wherein said precipitation agent comprises at least one selected from the group consisting of metal salt, lipid, and/or polymer.

15. The method of claim 12, wherein the second solution is added to the initial solution under low-frequency sonication to precipitate drug particles.

16. A drug particle formed according to the method of claim 1.

17. A method of forming drug particles, comprising:
providing a drug dissolved in an initial solution;
providing beads in the initial solution;
sonicating said initial solution of the dissolved drug using low-frequency sonication at a frequency of about 60 hertz to precipitate drug particles from said initial solution, wherein said low-frequency sonication causes said drug particles to precipitate with diameters ranging from about 100 nanometers to about 200 micrometers;
adding a second solution;
evaporating a portion of the initial and/or second solution; and
collecting said drug particles.

18. A method of forming drug particles, comprising:
providing an initial solution;
providing beads in the initial solution;
sonicating said initial solution using low-frequency sonication at a frequency of about 60 hertz;
stirring;
adding a drug dissolved in a second solution to the initial solution and maintaining the sonication using low-frequency sonication to precipitate drug particles from said second solution, wherein said low-frequency sonication causes said drug particles to precipitate with diameters ranging from about 100 nanometers to about 200 micrometers, and stirring;
evaporating a portion of the initial and/or second solution; and
collecting said drug particles.

19. A drug particle forming apparatus comprising:
a chamber for containing a drug dissolved in an initial solution;
a low-frequency vibration source for agitating said initial solution of the dissolved drug at a frequency of about 60 hertz to precipitate drug particles with diameters ranging in size from about 100 nanometers to about 200 micrometers;
at least one input port into said chamber for adding a second solution and/or a gas;
at least one output port near the top of said chamber for providing a vacuum and evaporating a portion of the initial and/or second solution; and
at least one output port from said chamber for collecting said drug particles.

20. A method of forming drug particles of a compound, comprising:
providing a compound dissolved in an initial solution;
sonicating the initial solution of the dissolved compound using low-frequency sonication at a frequency of about 60 hertz to precipitate particles of the compound from said initial solution, wherein said low-frequency sonication causes said particles of the compound to precipitate with diameters ranging from about 100 nanometers to about 200 micrometers;
evaporating a portion of the initial solution; and
collecting particles of the compound.

* * * * *

UNITED STATES PATENT AND TRADEMARK OFFICE
CERTIFICATE OF CORRECTION

| | | |
|---|---|---|
| PATENT NO. | : 8,501,232 B2 | Page 1 of 1 |
| APPLICATION NO. | : 10/512345 | |
| DATED | : August 6, 2013 | |
| INVENTOR(S) | : Talton et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1720 days.

Signed and Sealed this
Twenty-fourth Day of February, 2015

Michelle K. Lee
*Deputy Director of the United States Patent and Trademark Office*